(12) United States Patent
Shan et al.

(10) Patent No.: US 7,180,581 B1
(45) Date of Patent: Feb. 20, 2007

(54) LITHOGRAPHY FOR OPTICAL PATTERNING OF FLUIDS

(75) Inventors: Jerry W. Shan, Raritan, NJ (US); Paisan Atsavapranee, Cabin John, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 300 days.

(21) Appl. No.: 10/932,647

(22) Filed: Sep. 2, 2004

Related U.S. Application Data

(60) Provisional application No. 60/500,236, filed on Sep. 5, 2003.

(51) Int. Cl.
*G01P 3/36* (2006.01)
(52) U.S. Cl. .................................................. 356/28.5
(58) Field of Classification Search ................ 356/28.5
See application file for complete search history.

(56) References Cited

U.S. PATENT DOCUMENTS

| | | | | |
|---|---|---|---|---|
| 4,948,258 A | * | 8/1990 | Caimi | 356/603 |
| 5,333,044 A | * | 7/1994 | Shaffer | 356/28 |
| 6,386,050 B1 | * | 5/2002 | Yin et al. | 73/861.95 |

OTHER PUBLICATIONS

U.S. provisional Appl. No. 60/500,236, filed Sep. 5, 2003, invention entitled "Lithography for Optical Patterning of Fluids," joint inventors Jerry W. Shan and Paisan Atsavapranee.

M. M. Koochesfahani, "A Novel Method for Instantaneous, Quantitative Measurement of Molecular Mixing in Gaseous Flows," *Experiments in Fluids*, vol. 33, No. 1, pp. 202-209 (Jul. 2002; published online, Springer-Verlag, May 14, 2002).

D. G. Bohl, M. M. Koochesfahani, B. J. Olson, "Development of Stereoscopic Molecular Tagging Velocimetry," *Experiments in Fluids*, vol. 30, No. 3, pp. 302-308 (Mar. 2001).

B. Stier and M. M. Koochesfahani, "Molecular Tagging Velocimetry (MTV) Measurments in Gas Phase Flows," *Experiments in Fluids*, vol. 26, No. 4, pp. 297-304 (Mar. 1999).

(Continued)

*Primary Examiner*—Thomas H. Tarcza
*Assistant Examiner*—Luke D. Ratcliffe
(74) *Attorney, Agent, or Firm*—Howard Kaiser

(57) ABSTRACT

An illuminator (e.g., laser) produces a light beam that partially passes through, and is partially blocked by, a mask contrastingly patterned via non-transparent and transparent portions. The mask-conformed light passes through a lens so that the mask's pattern is projected into fluid seeded with a luminescent substance, which illuminatively reveals an image of the mask's pattern. The light beam can also be expanded and/or diffused prior to reaching the mask. Instead of or in addition to transmissive properties, the mask can have reflective properties wherein the illuminator-produced light beam partially bounces off of, and is partially absorbed by, a mask contrastingly patterned via non-reflective and reflective portions. Reflective optics can supplement or replace refractive optics for projecting the mask's pattern into the fluid. Indication of fluid flow and/or fluid concentration change is afforded through perceived distinctions between the illuminatively revealed images obtained at the same location at different times.

6 Claims, 4 Drawing Sheets

OTHER PUBLICATIONS

J.G. Santiago, S. T. Wereley, C. D. Meinhart, D. J. Beebe, R. J. Adrian, "A Particle Image Velocimetry System for Microfluidics," *Experiments in Fluids*, vol. 25, No. 4, pp. 316-319 (Sep. 1998).

C. P. Gendrich, M. M. Koochesfahani, and D. G. Nocera, "Molecular Tagging Velocimetry and Other Novel Applications of a New Phosphorescent Supramolecule," *Experiments in Fluids*, vol. 23, No. 5, pp. 361-372 (Nov. 1997).

Manoochehr Koochesfahani, Richard Cohn and Colin MacKinnon, "Simultaneous Whole-Field Measurements of Velocity and Concentration Fields Using a Combination of MTV and LIF," *Meas. Sci. Technol.*, vol. 11, No. 9, pp. 1289-1300 (Sep. 2000).

M. M. Koochesfahani, "Molecular Tagging Velocimetry (MTV): Progress and Applications," *AIAA Paper* AIAA-99-3786, invited, American Institute of Aeronautics and Astronautics, 30th AIAA Fluid Dynamics Conference, Norfolk, Virginia, Jun. 28, 1999-Jul. 1, 1999 (15 pages, including cover page).

Manoochehr M. Koochesfahani and Daniel G. Nocera, "Molecular Tagging Velocimetry Maps Fluid Flows," *Laser Focus World*, pp. 103-108 (Jun. 2001).

\* cited by examiner

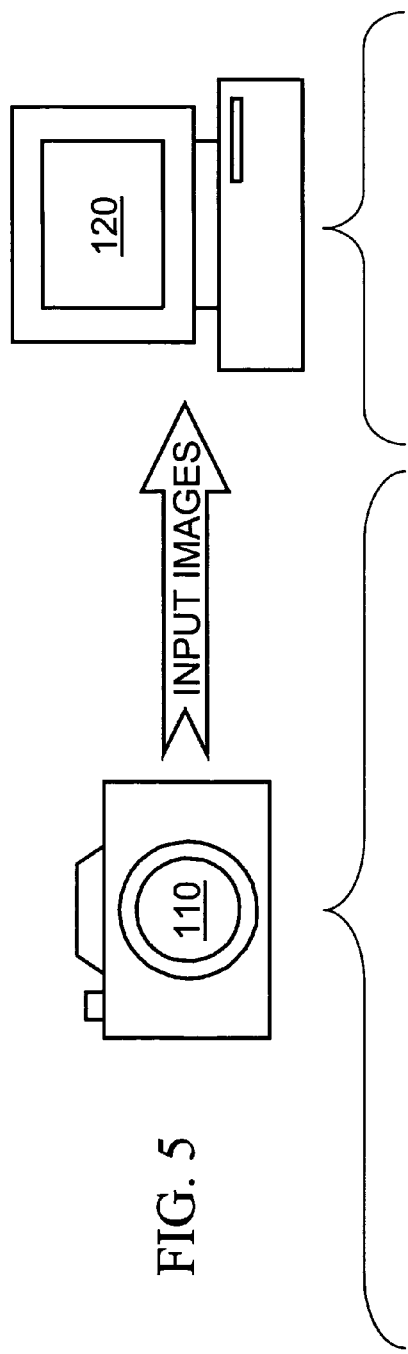
FIG. 3A
FIG. 3B
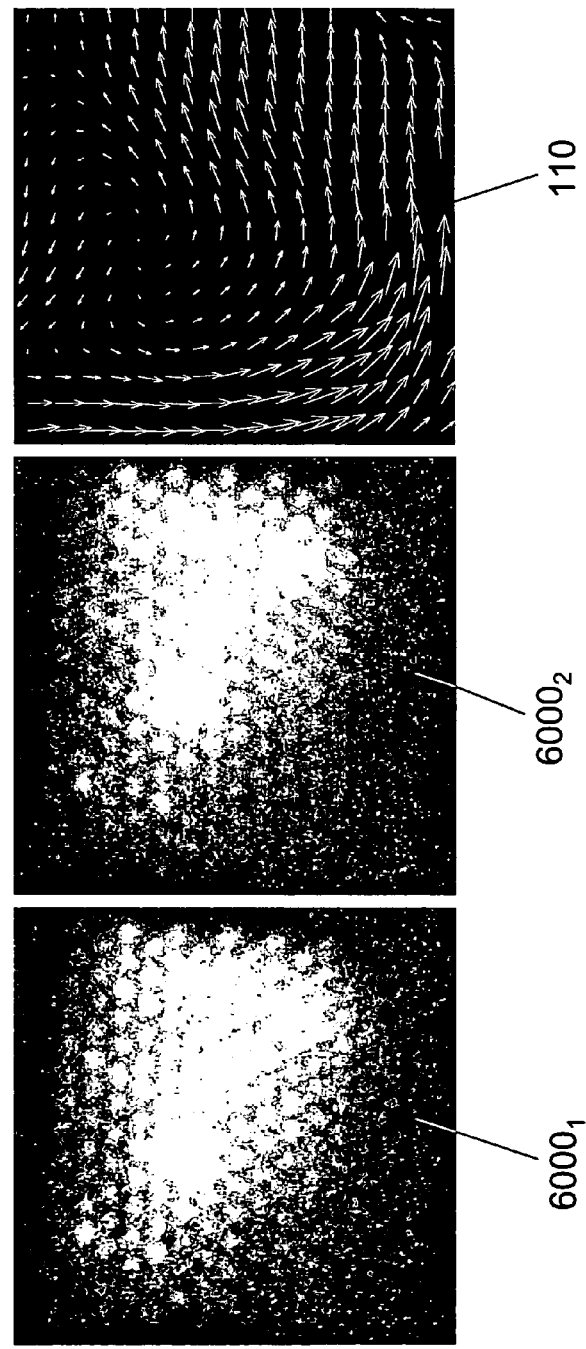
FIG. 4
FIG. 5

LITHOGRAPHY FOR OPTICAL PATTERNING OF FLUIDS

CROSS-REFERENCE TO RELATED APPLICATIONS

This application claims the benefit of U.S. provisional application No. 60/500,236, filed 5 Sep. 2003, hereby incorporated herein by reference, entitled "Lithography for Optical Patterning of Fluids," joint inventors Jerry W. Shan and Paisan Atsavapranee.

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to measurement pertaining to fluids, more particularly to methods and apparatuses for effecting measurement of the velocity or concentration of fluids using molecular tracing material.

According to the flow velocity measurement technique known as particle-image velocimetry (PIV), small seed particles are used to track the flow of a fluid. The particle seeding required for particle-image velocimetry can be undesirable or lead to inaccurate results in some situations. For example, seeding the flow medium at the density required to resolve the finest relevant length scales in complex flows may itself influence the flow dynamics. This can be the case in very-high Reynolds number turbulence (such as boundary layers on ships or submarines), or in micro-fluidic devices (wherein typical dimensions can approach the diameter of seed particles). In other situations, velocimetry techniques that rely upon particles can be inaccurate due to flow-tracking problems. These can arise when the fluid is strongly accelerated, and seed particles are density-mismatched with the fluid. See Adrian, R. J., "Particle-Imaging Techniques for Experimental Fluid Mechanics," *Annual Reviews in Fluid Mechanics*, vol. 23, 1991, pages 261–304, incorporated herein by reference. Heavy particles, for instance, can lag the fluid flow in shocks, and may be centrifuged out of vortex cores. Other flow tracking problems may arise in the presence of large temperature or electric-potential gradients (as in electro-hydrodynamic flows) due to thermophoretic and electrophoretic forces acting on the particles.

Molecular-tagging velocimetry, also known as laser-induced photochemical anemometry, is a flow velocity measurement technique that uses luminescent molecular tracers instead of particles to track the motion of moving fluids. See, e.g., the following references, each incorporated herein by reference: Gendrich, C. P., Koochesfahani, M. M. and Nocera, D. G., "Molecular Tagging Velocimetry and Other Novel Applications of a New Phosphorescent Supramolecule," *Experiments in Fluids*, volume 23, pages 361–372, 1997; Falco, Robert E. and Nocera, Daniel G., "Quantitative Multipoint Measurement and Visualization of Dense Solid-Liquid Flows by Using Laser Induced Photochemical Anemometry (LIPA)," *Particulate Two-Phase Flow*, M. C. Rocco, Ed., Butterworth-Heinemann, Boston, 1993, chapter 3, pages 59–126. Flow measurement using molecular tracers is desirable when techniques that rely upon seeding the fluid with small particles are unusable or deficient.

Molecular-tagging velocimetry uses molecular tracers rather than seed particles, thus representing a viable alternative to particle-image velocimetry. According to molecular-tagging velocimetry, flow tracers such as caged-fluorescent molecules or long-lifetime phosphorescent compounds are uniformly mixed with the flow medium and selectively excited with illumination at the appropriate wavelength. The excited regions, which luminesce, are imaged at two successive times. Lagrangian velocities in the flow are estimated from the displacement of the selectively excited regions. An important aspect of molecular-tagging velocimetry is its ability to selectively illuminate regions in the flow. This has been done in the past by illuminating single or multiple planes in the flow medium.

In order to measure two components of velocity in the practice of molecular-tagging velocimetry, the selective excitation of the flow medium must generate gradients in at least two (preferably orthogonal) directions. This has been done via the splitting and expanding of a laser beam into two sheets, and the blocking of each sheet with a comb-like beam blocker, such as shown in FIG. 5 of the aforementioned Gendrich et al. reference. Gendrich et al's FIG. 5 is a schematic illustrating a conventional illumination system for flow measurements. The region "tagged" by a grid pattern using beam blockers in this manner as disclosed by Gendrich et al. is shown in their FIG. 5 to be characterized by (approximate) uniformity of slot width and spacing. Examples of conventional beam-blockers are shown in Gendrich et al.'s FIGS. 4a and 4b. Gendrich et al.'s FIG. 4a shows 2 mm front-silvered mirror slivers glued to a steel substrate. Gendrich et al.'s FIG. 4b shows alternating 1.6 mm and 0.8 mm slots cut into 0.75 mm thick aluminium. The resulting grid pattern in the fluid can be used to make velocity measurements in two-dimensional plane.

A summary of illumination methods for molecular-tagging velocimetry is given by Koochesfahani, M. M., "Molecular Tagging Velocimetry (MTV): Progress and Applications," *AIAA Paper* AIAA-99-3786, invited, American Institute of Aeronautics and Astronautics, 30th AIAA Fluid Dynamics Conference, Norfolk, Va., 28 Jun.–1 Jul., 1999, incorporated herein by reference. Also of interest is Koochesfahani, Manochehr M. and Nocera, Daniel G., "Molecular Tagging Velocimetry Maps Fluid Flows," *Laser Focus World*, Jun. 2001, pages 103–108, incorporated herein by reference.

Existing flow-illumination procedures for practicing molecular-tagging velocimetry have several limitations, including the following. First, according to these existing techniques, the illumination ideally should come from a direction perpendicular to the viewing direction; this requires optical access to the flow from two different directions (one for viewing, one for illumination), which can be difficult to arrange in experiments. Moreover, the illumination pattern is limited to simple grids. Furthermore, diffraction from the beam blockers limits the minimum line width and spacing for the grid pattern; this limits the resolution of the flow measurement.

SUMMARY OF THE INVENTION

In view of the foregoing, it is an object of the present invention to provide improved method and apparatus for effecting illumination of a fluid or a selected portion thereof in a manner that is suitable for conducting molecular-tagging measurement of fluid flow.

The present invention's flow measurement system involves "lithographic" patterning of material volumes in fluids. The inventive lithographic system enables optical imprinting of arbitrary patterns in fluid media. When used on fluids seeded with photo-activated, luminescent tracer molecules, the present invention allows for selective flow visualization and optical measurement of velocity and concentration fields in fluid flows. The present invention's lithographic patterning of fluids is thus useful for effecting velocity measurements and/or mixing measurements.

"Lithography," as is conventionally known, is a two-hundred year old printing methodology that is based on the chemical repellence of oil and water (i.e., the inability of water and oil to mix together). Generally, a pattern (design) is drawn or painted, using an oily substance (e.g., oily crayon or oily paint), on an object having a flat surface (e.g., a stone or plate). The object's surface is moistened with water, which is accepted by the object's surface in areas not covered by the oily substance. An oily ink is applied to the object's surface, the ink adhering only to the pattern and being repelled by the water-wet areas of the plate. A print of the pattern is made by pressing paper against the inked pattern. The present inventors broadly characterize their invention as "lithographic" in nature insofar as a pattern is being transferred from one medium to another. According to the present invention, light is used to transfer a pattern from a mask to a luminescent tracer-seeded fluid medium.

The inventive method as typically embodied serves to illuminate fluid for purposes of facilitating flow visualization. The inventive method typically comprises transmitting light so as to: pass through and/or reflect from a mask; subsequently pass through and/or reflect from an optical system; and, subsequently pass into a fluid seeded with luminescent tracer material. Light is emitted, the mask patterns the emitted light, the optical system projects an image of the patterned light into the fluid, and at least some of the luminescent tracer material at least substantially manifests the image in the fluid. If transmissive in nature, the mask is characterized by a selected pattern of opaqueness and transparency. If reflective in nature, the mask is characterized by a selected pattern of opaqueness and reflectivity. The mask can be a device than is both transmissive and reflective in nature in that opaque portions along with transparent portions as well as reflective portions characterize the pattern. The optical system projects in said fluid an image characterized by the pattern. The image manifests in the fluid via the luminescent tracer material in a selected region of the fluid. The optical system of projecting an image can be refractive and/or reflective in nature. Any of various light sources can be used, such as a laser or an arc lamp. In order to effect flow visualization according to the present invention, the inventive method as typically embodied further comprises comparing the manner in which the image manifests in the fluid via the luminescent tracer material in the selected region at two different times. A change in the manifesting of the image indicates (i) a flow of the fluid and/or (ii) a change in concentration of the fluid.

Typical inventive apparatus is for illuminating a fluid having dispersed therein a multiplicity of luminescent (e.g., fluorescent or phosphorescent) tracer molecules. The inventive apparatus comprises light emission means, a mask device and projection means. The mask device, for masking the light emitted by the light emission means, has a pattern defined by partial transparency (and/or partial reflectivity) and partial opaqueness. The projection means is for projecting the masked light into a fluid so as to form an image of the pattern in the fluid. In association with the projected image, some tracer molecules luminesce in conformance with the pattern. According to inventive embodiments wherein the apparatus is further capable of determining the flow of the fluid, the apparatus further comprises means for comparing the manner in which some tracer molecules luminesce in association with said projected image on at least two different occasions. The comparison is indicative of variation in the flow of said fluid in the context of the projected pattern. The means for comparing includes a camera and/or computer.

Some preferred embodiments of inventive apparatus are characterized by axial alignment, both structurally and optically. For instance, according to some inventive embodiments the light emission means includes a laser device for emitting a light beam. The inventive apparatus further comprises a beam expander (for expanding the light beam emitted by the laser device) and a diffuser (for diffusing the light beam as expanded by the beam expander). The projection means includes refractive optics characterized by a geometric optical axis. The beam expander includes its own refractive optics characterized by its own geometric optical axis. The projection means' optical axis and the beam expander's optical axis coincide. The laser, the expander, the diffuser, the mask device and the refractive optical system are arranged so as to be at least approximately aligned along the shared geometric optical axis.

The present invention represents an improved methodology toward the optical patterning of fluids for velocity and/or mixing (e.g., concentration) measurements. In accordance with typical embodiments of the present invention, lithography is used to project an image of a mask into a fluid. The motion and mixing of material volumes of fluid particles can be tracked using photo-activated, long-lifetime lumiphores mixed in the fluid, such as caged fluorescent molecules or long-lifetime phosphorescent compounds. The lithographic patterning is scalable to submicron resolution for microflows, and the mask pattern can be easily optimized for the requirements of different experiments. Discussed hereinbelow are material volumes and derived Lagrangian velocities relating to inventive experimentation.

The present invention features, inter alia, the use of an optical system, such as a lens, to project an image of a mask into the flow of fluid. Advantageously, optical access to the flow is required from only one direction, as the illumination and viewing can be co-linear. Further, the illumination pattern is not limited to simple grids; the present invention's mask pattern can be varied in accordance with different flows and measurement objectives. In addition, practice of the present invention can achieve measurement resolutions that are significantly greater than those achieved through conventional practice.

Other objects, advantages and features of the present invention will become apparent from the following detailed description of the invention when considered in conjunction with the accompanying drawings.

BRIEF DESCRIPTION OF THE DRAWINGS

In order that the present invention may be clearly understood, it will now be described, by way of example, with reference to the accompanying drawings, wherein like numbers indicate the same or similar components, and wherein:

FIG. 3A and FIG. 3B are pictorial views, in accordance with the present invention, of a luminescent array of dots (such as shown in FIG. 2A) in a moving fluid at two different times. FIG. 3A shows I ($t=t_0$). FIG. 3B shows I ($t=t_0+2$ ms).

FIG. 4 is a computer-processed representation, in accordance with the present invention, of the measured flow field associated with FIG. 3A and FIG. 3B.

FIG. 5 is a diagrammatic representation, in accordance with the present invention, of how FIG. 3A, FIG. 3B and FIG. 4 collectively illustrate the photographing of the luminescent image by a camera (FIG. 3A and FIG. 3B) and the processing thereof by a computer (FIG. 4).

DETAILED DESCRIPTION OF THE INVENTION

Figure 1:
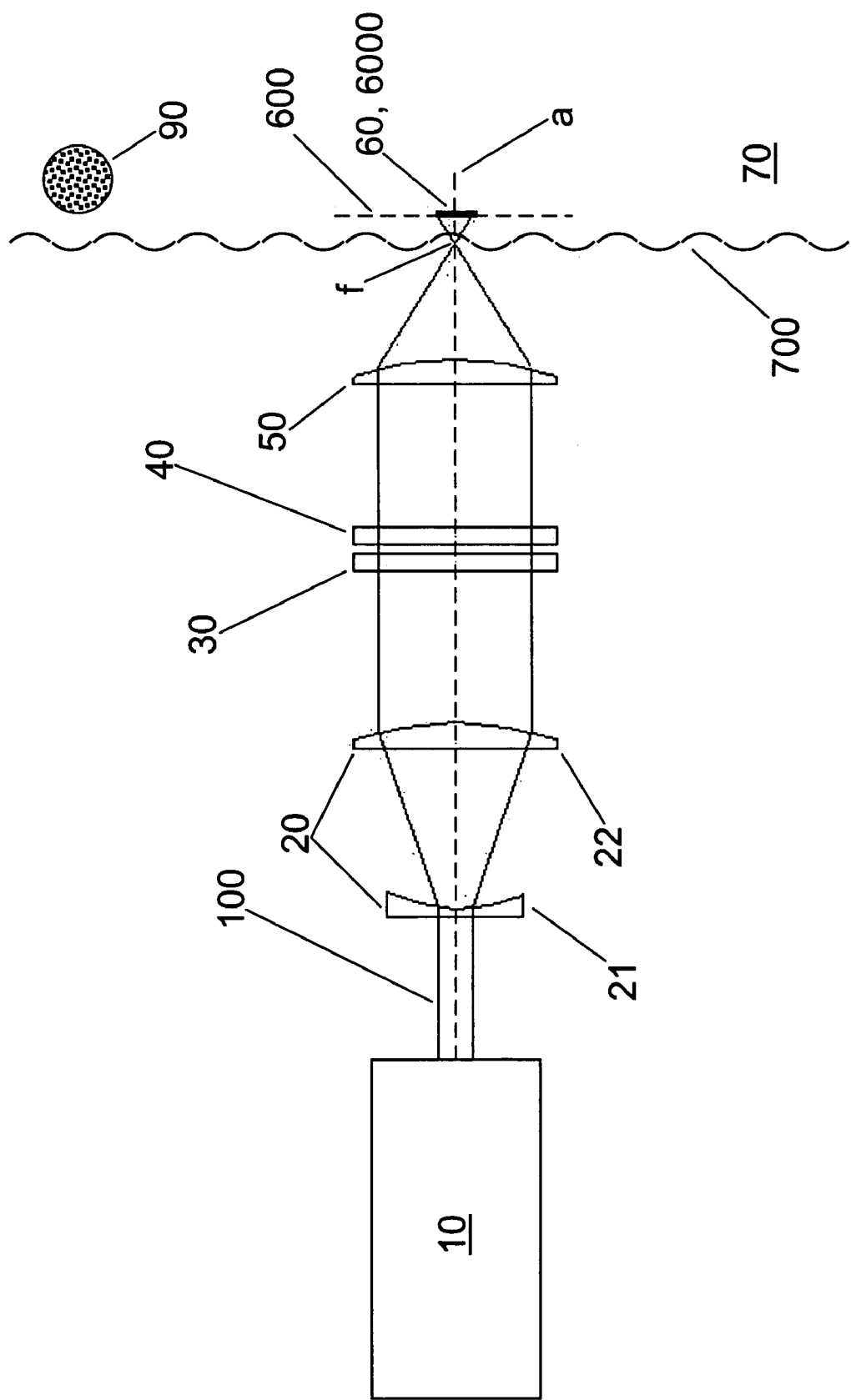
FIG. 1 is a schematic of an embodiment of the present invention's lithography system for optical patterning of fluid media for rendering flow and/or mixing measurements.

The present invention's lithography system is typically designed to optically pattern fluid flows for the purposes of performing velocity and/or mixing (e.g., concentration) measurements. Referring now to FIG. 1, the inventive system includes a light source 10, a beam expander 20, a diffuser 30, a mask 40 and image projection means 50. According to many preferred inventive embodiments, light source 10 is a laser, beam expander 20 includes two lenses 21 and 22, diffuser 30 is a transmitting diffuser (such as a ground-quartz-window transmitting diffuser), and projection means 50 includes a single lens. Demagnified image 60 is projected onto the geometric image plane 600 in fluid 70, located at or near the surface 700 of fluid 70. The selectively illuminated region in fluid 70 is that which is defined by luminescent image 6000.

As illustrated in FIG. 1, laser 10, lenses 20, ground-quartz-window transmitting diffuser 30, mask 40, lens 50, and demagnified image 60 are axially aligned along optical axis a. Fluid 70 is seeded with photo-activated, luminescent (e.g., fluorescent or phosphorescent) tracers 90. The light beam 100 from a laser 10 of appropriate wavelength to excite photoactive tracer molecules 90 is expanded with a set of lenses 20 and directed onto a ground-quartz-window diffuser 30. The expander 20 system is shown to include a plano-concave lens 21 (for diverging the light 100 rays) and plano-convex lens 22 (for converging the divergent light 100 rays so as to reestablish straight parallelism of light 100 rays). A mask 40 with a desired pattern (e.g., an array of dots) is placed in contact with or close to the diffuser 30 with the desired pattern. A lens 50 is used to project a demagnified image 60 of the mask 40 onto the image plane 600. Lens 50 is shown to be a single plano-covex lens that causes the light 100 rays passing therethrough to converge so as to meet at focal point f and project an image 60 beyond focal point f. The projected light image 60 describing image plane 600 excites luminescence in the tracers 90 with which the flow medium 70 is seeded, thereby forming in projection image plane 600 a luminescent image 6000 that is equivalent to or congruous with the projected image 60.

Depending on the inventive embodiment, mask 40 can be either transmissive or reflective in nature. A transmissive mask 40 is characterized by both optical transparency and optical opaqueness, wherein the transparent and opaque portions together define a pattern. For instance, mask 40 can include a transparent object imprinted with opaque material configured in a pattern, so that the transparent object and the opaque material in combination are capable of effectuating the pattern relative to light passing through mask 40. A reflective mask 40 is characterized by both optical reflectivity and optical opaqueness, wherein the reflective and opaque portions together define a pattern. For instance, mask 40 can include a reflective object imprinted with opaque material configured in a pattern, so that the reflective object and the opaque material in combination are capable of effectuating the pattern relative to light being deflected by mask 40.

Figure 2D:
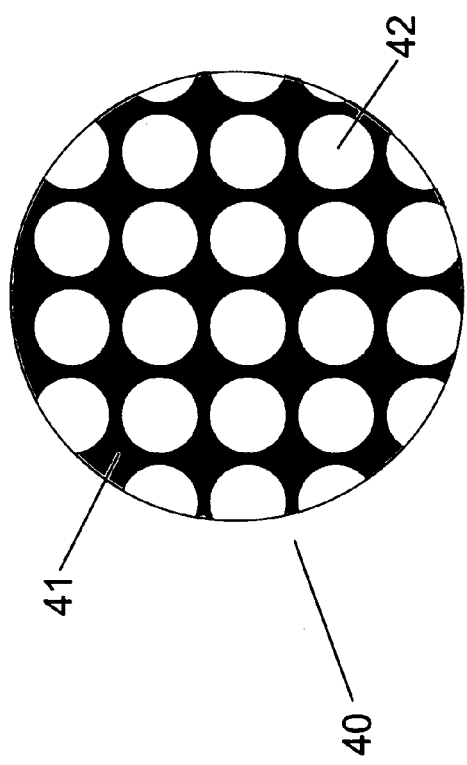
FIG. 2D is a diagrammatic representation of an example of a patterned mask, in magnified view showing a portion thereof, that can be inventively used for permitting the passage of light therethrough (or the reflection of light therefrom) so that an image of the resultant patterned configuration of light can be projected into a fluid of interest.
Figure 2C:
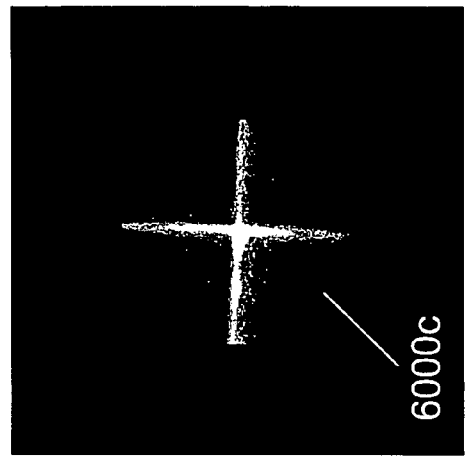
FIG. 2A, FIG. 2B and FIG. 2C are pictorial views, in accordance with the present invention, of various luminescent patterns created with projection lithography in still water seeded with a molecular tracer.
Figure 2B:
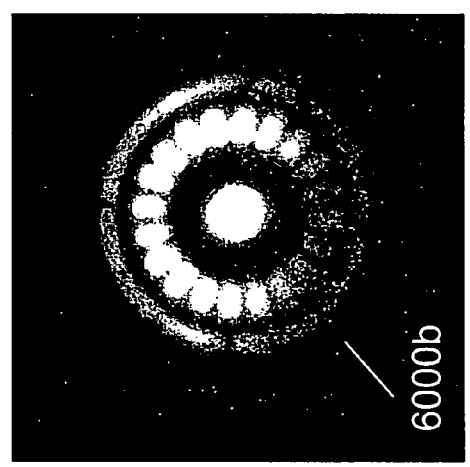
Figure 2A:
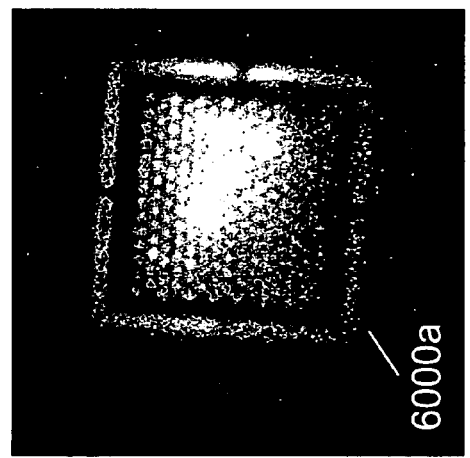

Reference is now made to FIG. 2A, FIG. 2B and FIG. 2C, which show examples of the respective luminescent images 6000 in non-flowing water 70 of various masks 40, viz., luminescent images 6000a, 6000b and 6000c, respectively. Luminescent images 6000 were photographed by the present inventors, in testing of their invention, using an imaging device such as digital camera 110 shown in FIG. 1. Regarding each of these figures, the projected light image 60 is a two-dimensional pattern with depth of focus $DOF = k \lambda/NA^2$, where $\lambda$ is the wavelength of illumination, NA is the numerical aperture of the optical system, and k is a system-dependent constant of order unity. The projected image 60 is used to excite luminescence in the fluid medium 70, resulting in luminescent image 6000. The mask 40 diagrammatically depicted in partial, enlarged view in FIG. 2D is provided with an array of transparent holes 41 (or reflective circles 41, if mask 40 is reflective rather than transmissive), in contrast with opaque area(s) 42, for bringing about a dot-array patterned luminescent image 6000 such as shown in FIG. 2A.

With reference to FIG. 3A, FIG. 3B, FIG. 4 and FIG. 5, when fluid 70 is in a flowing condition, changes (often subtle) are manifested over time in the luminescent image pattern 6000. One or more fluid 70 flow characteristics can be ascertained based on appreciable differences over time in tracer 90 luminescence; in essence, changes in fluid 70 flow are noted in the context of that portion of luminescent pattern 6000 which strictly corresponds to patterned image 60. Luminescent pattern 6000, was photographed by the present inventors (using camera 110) in fluid 70 on a first occasion; luminescent pattern 60002 was photographed by the present inventors at the same spatial location on a subsequent occasion. Computer 120 receives and processes the raw photographic luminescent images 6000 from camera 110. By recording the luminescent pattern 6000 at the same location in the fluid 70 flow at two different times, the Lagrangian flow velocity may be measured as $U(x,t) \approx \Delta X(x,t)/\Delta t$, where $\Delta$ is the displacement of the molecular marker, located at x at time t, over a short time interval $\Delta t$.

FIG. 4 shows a vector map 110, obtained by the present inventors as was processed by a computer 120, of the flow field associated with FIG. 3A and FIG. 3B. The raw photographic luminescent images 6000 (such as shown in FIG. 3A and FIG. 3B) were processed for velocity fields using cross-correlation software that finds the best match between the displaced luminescent patterns 6000, and 60002, resulting in a vector map 110 (such as shown in FIG. 4). Other quantities derived from the velocity field, such as vorticity, circulation and strain rate, can also be inferred, typically using a computer 120 having suitable software resident in its memory. The concentration and mixing of the tracer molecules 90 that are excited can also be inferred (e.g., using a computer 120) from the luminescence intensity, based upon knowledge of the dependence of intensity on the flow-tracer concentration.

The present invention's lithographic patterning of fluid is unique. In practicing the present invention's method and apparatus, which are novel, known analytical techniques can be adapted to inventive purposes. Of particular note is that, as pointed out hereinabove, information such as velocity fields can be derived from luminescent images in accordance with the present invention. In this regard, the digitally recorded images can be analyzed using software that finds the displacement field that results in the best match between two time-sequential images. To elaborate, for each subsection of the image pair, the cross-correlation function is computed. The spatial location of the peak of the cross-correlation function gives the displacement of the local features in that part of the image. For example, a peak centered at "(10,1)" means that the features within the first image of the pair have been displaced by ten pixels in the x direction and one pixel in the y direction in the time interval $\Delta T$ between images. The magnitude of the peak is of no import; only the location of the peak is germane to determining the displacement field which best maps one image to a subsequent image.

Thus, this type of image analysis is computationally implemented by calculating local spatial cross-correlations between two time-sequential images. The locations of the peaks of the cross-correlation functions are used to estimate the displacement field that best maps one image to another. This image analysis technique is available in commercial software packages and has been described in the literature; see, e.g., C. E. Willert and M. Gharib, "Digital Particle Image Velocimetry," *Exp. in Fluids* 10, pages 181–193, 1991, incorporated herein by reference. The image pair shown in FIG. 3A and FIG. 3B was processed by the present inventors using DaVis (LaVision GmBH, Goettingen, Germany) to generate the vector map 110. Alternative commercial packages for the cross-correlation image analysis include Insight 6 from TSI (Shoreview, Minn.) and FlowMap from Dantec Dynamics (Skovlunde, Denmark). Hence, in order to analyze image data, inventive practice can involve the use of same or similar image-analysis software and procedures that have been used in association with particle-image velocimetry.

Figure 6:
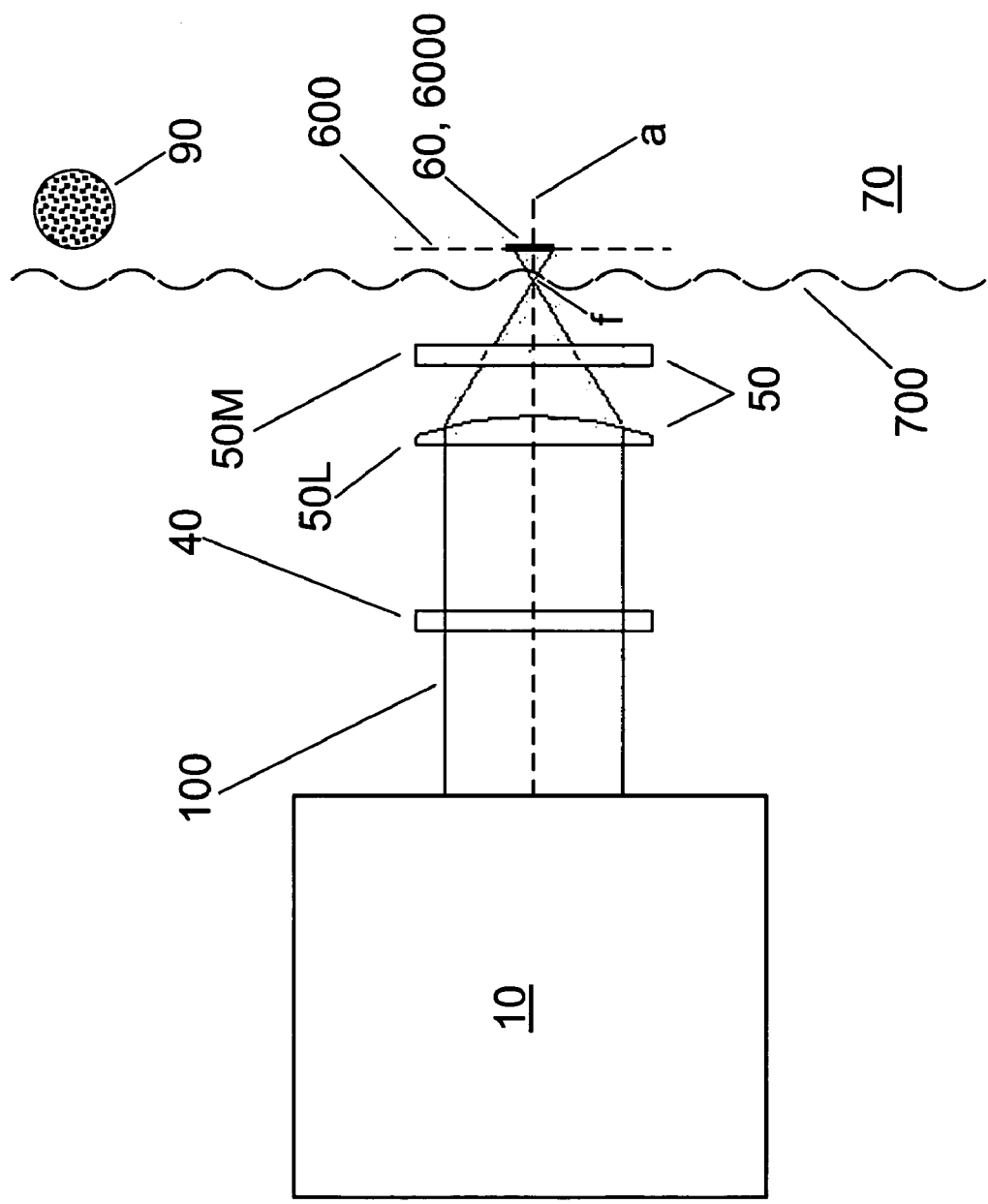
FIG. 6 is a schematic of another embodiment of the present invention's lithography system for optical patterning of fluid media for rendering flow and/or mixing measurements.

A key distinguishing feature of the inventive system as typically embodied is its use of an optical lens system 50 to project an image 60 of a mask 40 into the fluid 70 flow. The present invention's new approach is quite different from the conventional approach, which uses beam-blockers to generate shadows in a collimated light sheet. There are several advantages to the inventive approach. For instance, according to inventive practice, optical access to the flow is required from only one direction, as the illumination and viewing can be co-linear such as depicted in FIG. 1 and FIG. 6. Moreover, according to inventive practice, the illumination pattern is not limited to simple grids. The mask 40 pattern can be readily optimized for different flows and measurement purposes, such as demonstrated by the inventive examples shown in FIG. 3A, FIG. 3B and FIG. 4.

Furthermore, the measurement resolution associated with inventive practice can be significantly enhanced in comparison with the measurement resolution associated with conventional practice utilizing beam-blockers, which are limited by Fraunhoffer diffraction effects. The resolution limit, $d_{min}$ of the present invention's novel projection lithography system is $d_{min} = k \lambda / NA$, where NA is the numerical aperture, $\lambda$ is the illumination wavelength, and k is a system-dependent constant of order unity. According to inventive practice, the resolution is increased by the addition of the high-numerical-aperture lens, which projects an image of the mask onto the flow. For light at $\lambda = 266$ nm, and a typical optical system with k=1 and NA=0.3, the theoretical measurement resolution would be 0.9 microns.

Referring again to FIG. 1 and also to FIG. 6, there are various alternative embodiments of the present invention. For instance, rather than be a laser, light source 10 can be an alternative light source of the appropriate wavelength, such as an arc lamp. Beam expander 20 is shown in FIG. 1 to include at least two beam-shaping lenses; instead of including refractive optics, beam expander 20 can include reflective optics (e.g., at least two beam-shaping reflectors). According to some inventive embodiments, beam expander 20 is omitted altogether, such as shown in FIG. 6. Rather than include ground quartz, transmitting diffuser 30 can be of a kind that includes PTFE (Polytetrafluoroethylene), opal glass, ground-fused silica or other transmitting diffuser material. Diffuser 30 is shown in FIG. 1 to be a transmitting diffuser 30; instead of being a transmitting diffuser, diffuser 30 can be a reflective diffuser. According to some inventive embodiments, diffuser 30 is omitted altogether, such as shown in FIG. 6. The optical projection means 50 can include a single lens or plural lenses (e.g., a multi-element lens), and can include one or more mirrors in addition to or in alternative to one or more lenses. For instance, a dichroic mirror 50M, such as shown in FIG. 6, can be inserted in between a lens 50L and the image plane 600 to turn the optical axis a and permit co-linear illumination and imaging. A variety of long-lifetime phosphorescent compounds or caged-fluorescent molecules can be used for photo-activated, luminescent tracers 90, which are depicted in a magnified view in FIG. 1 and FIG. 6. The images can be processed for displacement (e.g., implementing a computer 120) through the use of feature-based particle tracking methods instead of correlation-based pattern recognition.

The present invention is not to be limited by the embodiments described or illustrated herein, which are given by way of example and not of limitation. Other embodiments of the present invention will be apparent to those skilled in the art from a consideration of this disclosure or from practice of the present invention disclosed herein. Various omissions, modifications and changes to the principles disclosed herein may be made by one skilled in the art without departing from the true scope and spirit of the present invention, which is indicated by the following claims.

What is claimed is:

1. Apparatus for illuminating a fluid having dispersed therein a multiplicity of luminescent tracer molecules, said apparatus comprising:

light emission means, said light emission means including a laser device for emitting a light beam;

a beam expander for expanding said emitted light beam, said beam expander including first refractive optics, said first refractive optics being characterized by a first geometric optical axis;

a mask device for masking said expanded light beam; and projection means for projecting said masked light beam into a fluid so as to form an image of said pattern in said fluid, said projection means including second refractive optics, said second refractive optics being characterized by a second geometric optical axis;

said first geometric optical axis and said second geometric optical axis being coincident, said first geometric optical axis and said second geometric optical axis thereby defining a common geometric optical axis;

said laser device, said mask device and said second refractive optics being arranged so as to be at least approximately aligned along said common geometric optical axis;

said laser device being capable of a emitting a laser beam along said common geometric optical axis;

wherein, in association with said projected image, some said tracer molecules luminesce in conformance with said pattern.

2. The apparatus of claim 1, wherein said mask device permits the passage of some said expanded light beam therethrough, said mask device having a pattern defined by partial transparency and partial opaqueness.

3. The apparatus of claim 1, wherein:

said apparatus further comprises a diffuser for diffusing said expanded light beam, said mask device masking said expanded and diffused light beam; and said laser device, said first refractive optics, said diffuser, said mask device and said second refractive optics are arranged so as to be at least approximately aligned along said common geometric optical axis.

4. The apparatus of claim 1, wherein said apparatus is further for determining the flow of said fluid, and wherein said apparatus further comprises means for comparing the manner in which some said tracer molecules luminesce in association with said projected image on at least two different occasions, said comparing being indicative of, in the context of said projected image, at least one of the following:

flow of said fluid;

change in concentration of said fluid.

5. The apparatus of claim 4, wherein said means for comparing includes at least one of a camera and a computer.

6. The apparatus of claim 1, wherein said laser device, said first refractive optics, said mask device and said second refractive optics are arranged so as to be at least approximately aligned along said common geometric optical axis.

* * * * *